United States Patent [19]

Makino et al.

[11] Patent Number: 5,138,166
[45] Date of Patent: Aug. 11, 1992

[54] MEDICAL X-RAY IMAGE DETECTING DEVICE

[75] Inventors: Takao Makino; Keisuke Mori, both of Kyoto, Japan

[73] Assignee: Kabushiki Kaisha Morita Seisakusho, Kyoto, Japan

[21] Appl. No.: 779,830

[22] Filed: Oct. 21, 1991

[30] Foreign Application Priority Data

Nov. 26, 1990 [JP] Japan ................................ 2-124689

[51] Int. Cl.⁵ ............................ A61B 6/14; G01T 1/20
[52] U.S. Cl. ........................................ 250/368; 378/40; 250/366
[58] Field of Search ............... 250/368, 366; 378/191, 378/38, 39, 40

[56] References Cited

U.S. PATENT DOCUMENTS 4,303,860  12/1981  Bjorkholm et al. ................. 250/368
4,878,234  10/1989  Pfeiffer et al. ........................ 378/40
5,008,547   4/1991  Molteni et al. ..................... 250/368

Primary Examiner—Carolyn E. Fields
Attorney, Agent, or Firm—Koda and Androlia

[57] ABSTRACT

A medical X-ray image detecting device wherein the fluorescent surface of a narrow belt-shaped X-ray fluorescen plate which emits light at the time of irradiation of X-ray through a slit is divided to rectangular units, optical fiber bundles are distributed alternately right and left and arranged vertically, the one end surface of each optical fiber bundle is attached to one of the divided fluorescent surface unit, the other end surface of each optical fiber bundle is attached to the image pickup surface of a solid-state image pickup device to make image formation possible, and the solid-state image pickup device is disposed behind an X-ray shielding member by which the slit is formed.

3 Claims, 4 Drawing Sheets

MEDICAL X-RAY IMAGE DETECTING DEVICE

BACKGROUND OF THE INVENTION

1. Field of the Invention

The present invention relates to improvements in an X-ray image detecting device for detecting X-ray penetration images using solid-state image pickup devices in a panoramic X-ray diagnosis apparatus for medical treatment, particularly for dental treatment.

2. Prior Art

Panoramic X-ray diagnosis apparatuses for medical treatment, particularly for dental treatment are widely used clinically to observe the arrangement of the teeth and the conditions of the dental roots in the mouth of a patient. As an example of such apparatuses, a panoramic photographing apparatus which performs panoramic radiographing by rotating an image detecting device and an X-ray source while maintaining a constant relationship between the image detecting device and the X-ray source, with the head of the patient positioned therebetween, is widely used for dental treatment. A conventional panoramic radiographic apparatus optochemically formed images of penetrated X-ray on X-ray sensitive films. This method took a long time for development and was not suited for immediate observation and diagnosis during treatment.

To solve this problem, an art is used for a dental radiographing apparatus to reproduce X-ray penetration images on a monitor unit by receiving slit-passed X-ray on a fluorescent plate to first obtain a visible light image, by forming the image on the image pickup surface of a pickup tube or a CCD image pickup device via an optical lens system and by converting the image to an electric signal. In addition, another art which directly and optically combines a fluorescent surface and an image pickup surface by using optical fiber and transmits images, instead of forming images by using an optical lens system, has been developed.

A prior art related to the above-mentioned technology has been disclosed, in the case of radiographing only one tooth and its surrounding area by using an apparatus (I) which receives X-ray beams from an X-ray source outside the mouth and picks up the beams as a still image by using an arrangement wherein a sensor comprising optical fiber which optically combines an X-ray fluorescent plate and the image pickup surface of an electronic chip, such as a CCD image pickup device, is disposed behind the tooth to be photographed in the mouth (Japanese Laid-open Patent Application No. 60-234645).

Another panoramic radiographing apparatus (II) discloses an art which combines the fluorescent surface image extending in the longitudinal direction of the above-mentioned slit on a small image pickup surface by gradually reducing the diameter of each element of the optical fiber (used to connect a narrow belt-shaped fluorescent surface to a CCD image pickup device) in the direction from the fluorescent surface to the image pickup surface of the CCD image pickup device (FIG. 2 in Japanese Laid-open Utility Model Application No. 63-140907). A third apparatus (III) discloses an art wherein the one end of the optical fiber bundle connected to the fluorescent surface extending in the longitudinal direction of the slit is cut at the surface obliquely to the axis of each element of the fiber bundle and the other end of the fiber bundle is cut at the surface orthogonally to the axis and connected to the image pickup surface of the CCD image pickup device, thereby the image on the fluorescent surface in the longitudinal direction of the slit is reduced and formed on the CCD image pickup device (FIG. 3 in Japanese Laid-open Utility Model Application No. 63-140907 cited above). With these apparatuses (II) and (III), the narrow belt-shaped fluorescent surface is connected via a fiber bundle to the image pickup surfaces of a plurality of CCD image pickup devices and the image signals from the CCD image pickup devices are electrically combined to obtain an X-ray panoramic image on the display screen of a monitor unit.

The above-mentioned solid-state image pickup device, such as a CCD image pickup device, wherein the image pickup surface of the solid-state image pickup device, is connected to an optical fiber bundle, X-ray transmits a visible light image to be formed on the fluorescent surface and the image is observed on the display screen on a monitor unit, has an image pickup surface size of about 5 mm square. This value is far smaller than the longitudinal length (about 150 mm) of the fluorescent surface. It is very difficult to increase the size of the image pickup surface. Even if possible, the cost is assumed to be excessive.

When using the prior art applied to the apparatus (I) for a panoramic radiographing apparatus, its image pickup surface is too small, and all ranges including the upper and lower jaw sections cannot be photographed. When using the art applied to the apparatus (II), it is difficult to uniformly taper (gradually reduce the diameter) the end of each element of the fiber. Even if possible, production cost would be excessive.

As a problem common to both the apparatuses (II) and (III), if the reduction ratio between the image on a divided fluorescent surface and the image formed by the fiber bundle on the image pickup surface of the CCD image pickup device is made larger, the resolution of the image signal from the CCD image pickup device is deteriorated.

In the case of all above-mentioned prior arts, since the solid-state image pickup devices are disposed in the penetration range of the slit-passing X-ray, the electric charges by X-ray irradiation inside the devices accumulate, being in danger of causing the solid-state image pickup devices to break.

The rim of the sealing material for the solid-state image pickup device is generally larger than the image pickup surface thereof and protrudes from the surface. If a plurality of image pickup devices are placed side by side, the rim of the sealing material for a solid-state image pickup device makes contact with the adjacent fiber bundles and the rims of the sealing materials for other adjacent solid-state image pickup devices, causing a problem when arranging the solid-state image pickup devices in an X-ray image detecting device.

SUMMARY OF THE INVENTION

In view of solving the above-mentioned problems, it is an object of the present invention to provide a medical X-ray image detecting device which uses solid-state image pickup devices to obtain a panoramic X-ray image of the entire jaw sections ranging from the upper to lower jaw bones without reducing the resolution of the image.

Another object of the present invention is to prevent the solid-state image pickup devices from being damaged by irradiated X-ray during panoramic photographing and to ensure easy arrangement of the solid-state image pickup devices in the apparatus.

For these purposes, the present invention uses fiber bundles which are not specially processed (tapered for example) to optically connect the fluorescent surface of the narrow belt-shaped fluorescent plate to the image pickup surfaces of a plurality of solid-state image pickup devices. By using the fiber bundles, the image on the fluorescent surface, at least the length of which in the longitudinal direction of the fluorescent surface is equal to the image pickup surface of the solid-state image pickup device, is projected to the image pickup surfaces of the solid-state image pickup devices. The image signals from a plurality of the solid-state image pickup devices are electrically combined to form images on the narrow belt-shaped fluorescent surfaces. Then in synchronization with the rotation of the fluorescent surfaces around the dental arch, the images on the fluorescent surfaces are electrically combined on the monitor screen to conduct curved tomographic photographing which provides an overall view of the entire dental arch as a panoramic image.

DETAILED DESCRIPTION OF THE INVENTION

Figure 1A:
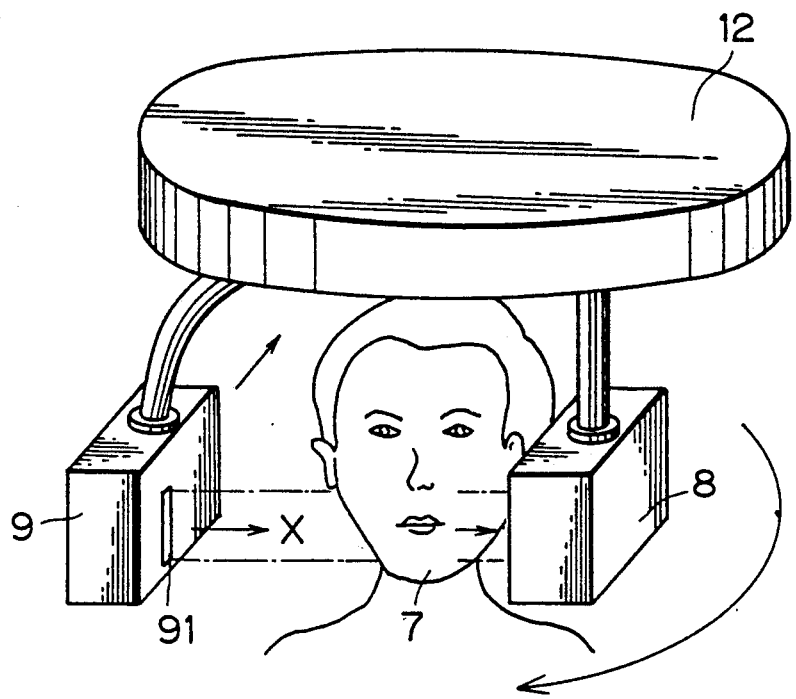
FIG. 1 (A) is an overall view of a dental X-ray panoramic diagnosis apparatus which incorporates the X-ray image detecting device of the present invention, FIG. 1 (B) is a partially cutaway perspective view of the X-ray image detecting device, FIG. 2 (A) is a traverse plan view of the X-ray image detecting device according to the present invention, FIGS. 2 (B) and 2 (C) are partially perspective views of the X-ray image detecting device, and FIGS. 3 (A), 3 (B) and 3 (C) are three different arrangement views of optical fiber bundles of other embodiments of the present invention.

The present invention provides a medical X-ray image detecting device comprising a narrow belt-shaped X-ray fluorescent plate disposed behind a slit formed by an X-ray shielding member, a plurality of optical fiber bundles, with the one end surface of each of the optical fiber bundles being attached to the fluorescent surface of the fluorescent plate, and solid-state image pickup devices, with the other end surface of each of the optical fiber bundles being attached to the image pickup surface of one of the image pickup devices. The X-ray image detecting device is characterized in that the fluorescent surface is divided in the longitudinal direction thereof into a plurality of rectangular units, the total length of which is the same as the vertical length of the image pickup surface of the image pickup device, the one end surface of each of the optical fiber bundles is attached to one of the divided fluorescent surface units to make individual image formation possible, and the bundles are distributed alternately right and left in the longitudinal direction, the other end surface of each of the fiber bundles is attached to the image pickup surface of one of the image pickup devices disposed on the right/left side at the backward position of the fluorescent surface unit and behind the X-ray shielding member to make individual image formation possible, whereby the X-ray image on the whole fluorescent surface is detected by combining individual image signals obtained from the solid-state image pickup devices.

In the present invention, the narrow belt-shaped fluorescent surface is divided in its longitudinal direction into a plurality of rectangular units by using the vertical length of the image pickup surface of a single solid-state image pickup device as one unit to be divided, and each solid-state image pickup device corresponding to one of the divided fluorescent surface units is connected by the optical fiber bundle. The image projected on the image pickup surface of each solid-state image pickup device is thereby not reduced. Since it is easy to make the diameter of the optical fiber element sufficiently smaller than the diameter of the picture element of the solid-state image pickup device, the resolution of the image is not made lower than that of the solid-state image pickup device.

In addition, since the optical fiber bundles are distributed alternately right and left in the longitudinal direction behind the fluorescent surface unit divided as mentioned above, the solid-state image pickup devices connected to the individual optical fiber bundles are vertically aligned at the distributed right-side and left-side fiber bundle positions behind the fluorescent plate (in one line on each side) of the fluorescent plate. A space is thus provided between adjacent optical fiber bundles. Therefore, even if the rims of the sealing material for the solid-state image pickup device protrude the image pickup surface of the solid-state image pickup device around the circumference of the device, the protruded sections of the solid-state image pickup devices connected to the optical fiber bundles do not contact each other, thereby allowing the solid-state image pickup devices to be disposed and arranged easily in the X-ray image detecting device.

EXAMPLES

Examples of the present invention are described below referring to the accompanying drawings.

Figure 1B:
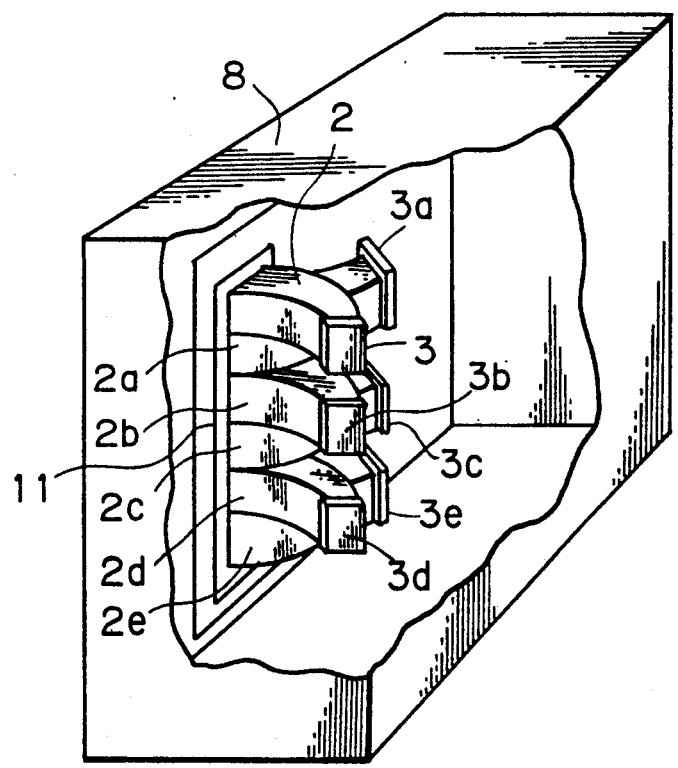

FIG. 1 (A) is an overall view of a dental panoramic X-ray diagnosis apparatus which incorporates the X-ray image detecting device of the present invention. This diagnosis apparatus is structured so that an X-ray source 9 incorporating an X-ray tube and a photographing box 8 incorporating the X-ray image detecting device of the present invention rotate around the jaw section 7 of a patient while an opposed positional relationship is maintained between the X-ray source 9 and the photographing box 8. The X-ray beam X irradiated from the slit 91 of the X-ray source 9 penetrates the jaw section 7 and reaches the slit 83 of the photographing box 8.

FIG. 1 (B) is a partially cutaway perspective view of an example of the X-ray image detecting device of the present invention incorporated in the photographing box 8. This example is detailed referring to FIGS. 2 (A), 2 (B) and 2 (C).

Figure 2A:
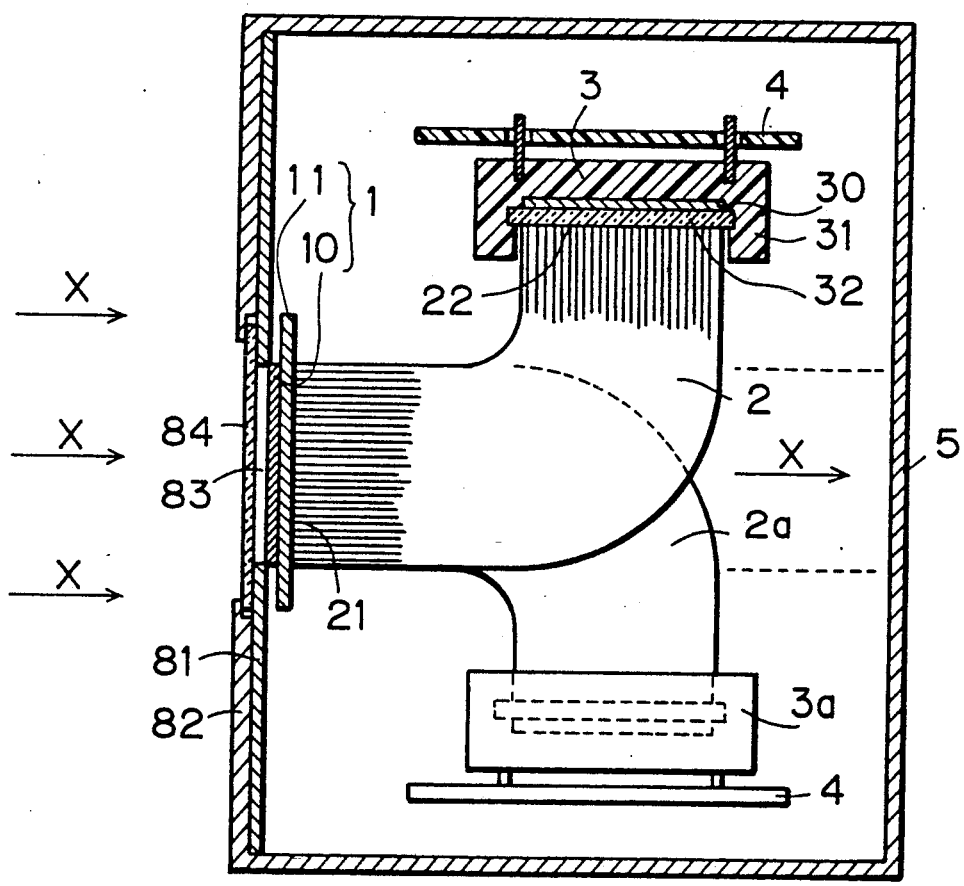
Figure 2B:
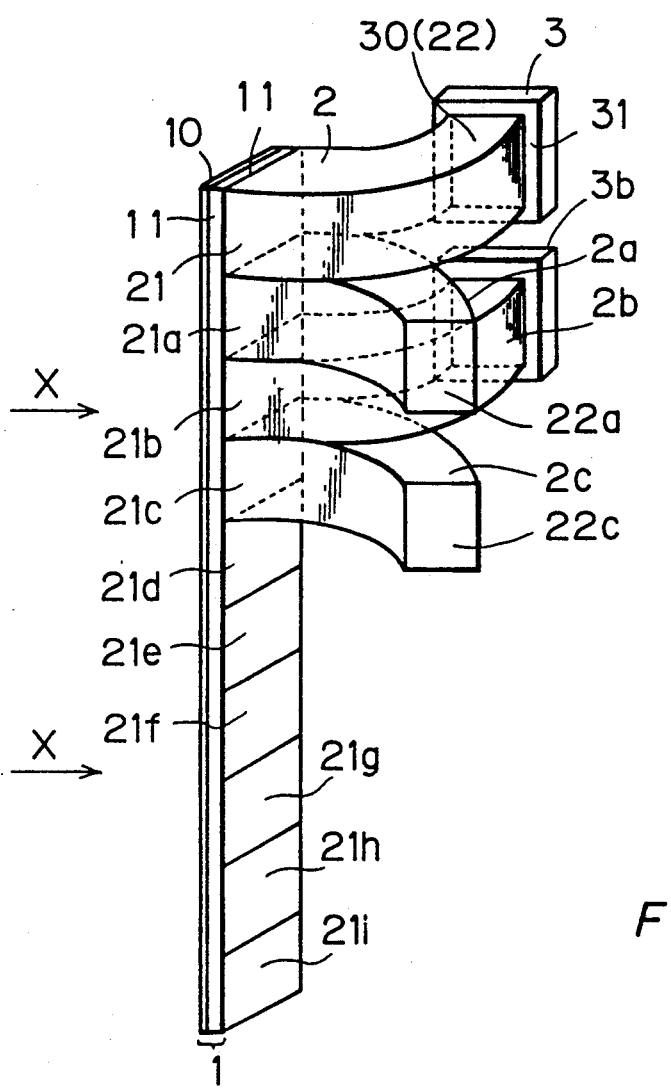
Figure 2C:
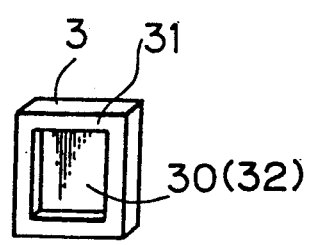

FIG. 2 (A) is a traverse plan view of the photographing box 8. Numeral 82 in the figure represents a steel plate used to form the photographing box 8. Numeral 81 represents a lead plate provided with a slit 83 (about 7×150 mm) and is used to shield the X-ray. Numeral 84 represents a black opaque plate disposed in front of the slit 83 to shield visible light. Behind the slit 83, a rectangular narrow belt-shaped fluorescent plate 1 is secured. A fluorescent material layer 10 which emits visible light when stimulated by X-ray is coated on the surface of the transparent glass substrate 11 of the fluorescent plate 1, thereby forming a fluorescent surface 10. The back side of the glass substrate 11 is attached to the end surface 21 of an optical fiber bundle 2 to make optical connection to the fluorescent surface 10.

The other end surface 22 of the fiber bundle 2 is connected to the image pickup surface 30 of a CCD image pickup device 3 via a protection glass plate 32 in the case of this example to make image formation possible. The optical fiber bundle 2 is bent nearly orthogonally almost in the middle of its route. The CCD image pickup device 3 is disposed outside the incident X-ray range at the backward position of the glass substrate 11 of the fluorescent plate 1 and behind the X-ray shielding plate 81 so that the device 3 is not adversely effected or damaged by the X-ray which passes the slit 83. Numeral 5 represents a lead plate used to shield the penetrated X-ray.

FIG. 2 (B) is a partially perspective view of the X-ray image detecting device and illustrates a mutual arrangement relationship among the fluorescent plate, the optical fiber bundles and the CCD image pickup device in the photographing box 8. In this figure, the fluorescent plate 1 is divided to ten sections in the longitudinal direction. The end surfaces 21, 21a, 21b, 21c, ... of the ten optical fiber bundles 2, 2a, 2b, 2c, ... corresponding to the ten sections are optically connected to the divided fluorescent surface units of the glass substrate 11. The optical fiber bundles 2, 2a, 2b, 2c, ... are bent nearly orthogonally almost in the middle of their routes so that they are alternately distributed right and left with respect to the incident direction of the incident X-ray.

The image pickup surfaces 30 of the CCD image pickup devices 3, 3a, 3b, ..., shown in FIG. 2 (C) are optically connected and attached to the other end surfaces 22, 22a, 22b, 22c, ... of the optical fiber bundles 2, 2a, 2b, 2c, ... respectively via the protection glass plates 32 to make image formation possible. Both end surfaces 21 and 22 of the optical fiber bundle 2 are cut orthogonally to the axis of the fiber and attached to the glass substrate 11 of the fluorescent plate 1 and the glass protection plate 32 of the CCD image pickup device 3 respectively so that images to be obtained are not magnified or reduced and are free from image distortion when the optical fiber bundle 2 transmits the image on the fluorescent surface 10 to the image pickup surface 30 of the CCD image pickup device 3.

In addition, since the CCD image pickup devices 3, 3a, 3b, ... are alternately distributed right and left, they do not cause any problem in their disposition, even when rims 31 made by the protruded sealing material of the CCD image pickup device 3 protrude and extend from the circumferences of the image pickup surfaces.

With this example, the X-ray image detecting device of the present invention is applied to a dental panoramic X-ray diagnosis apparatus. In this case, the longitudinal direction of the fluorescent surface 10 of the image pickup device incorporated in the photographing box 8 is vertical. A plurality of fluorescent surface units are disposed in the vertical direction, and the fiber bundles 2 corresponding to the fluorescent surface units are arranged in the vertical direction and alternately distributed right and left in the middle of their routes. The outgoing end surfaces of the fiber bundles 2 are respectively attached to the image pickup surfaces of the individual solid-state image pickup devices located in the same ranges corresponding to the vertically divided fluorescent surface units.

When applying the present invention to general medical panoramic radiographing apparatuses, the X-ray image detecting device of the present invention is moved laterally or rotationally with respect to the slit 83 to tomographically photograph planes or tomographically photograph curved surfaces other than dental arches. In this way, the X-ray image detecting device of the present invention can be used for general medical panoramic radiographing apparatuses by simply changing the relative positions and the movement direction of the X-ray source and the X-ray image detecting device, without changing the structure of the X-ray image detecting device.

Figure 3A:
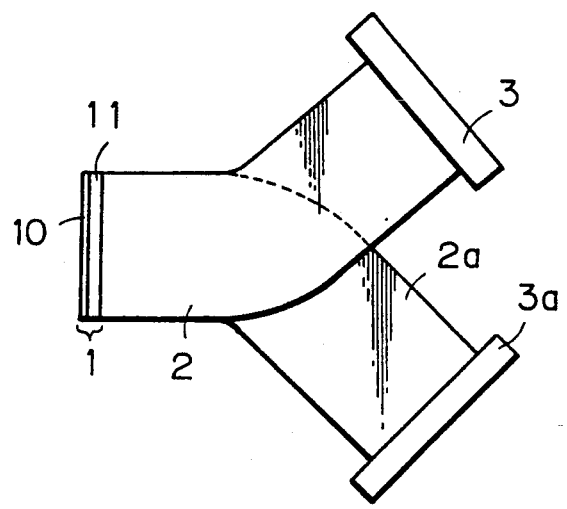
Figure 3B:
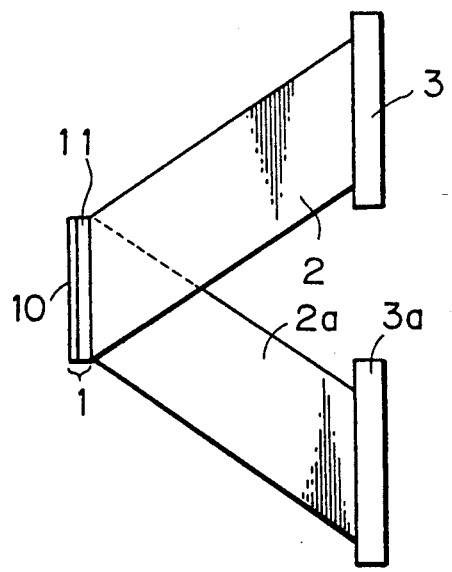
Figure 3C:
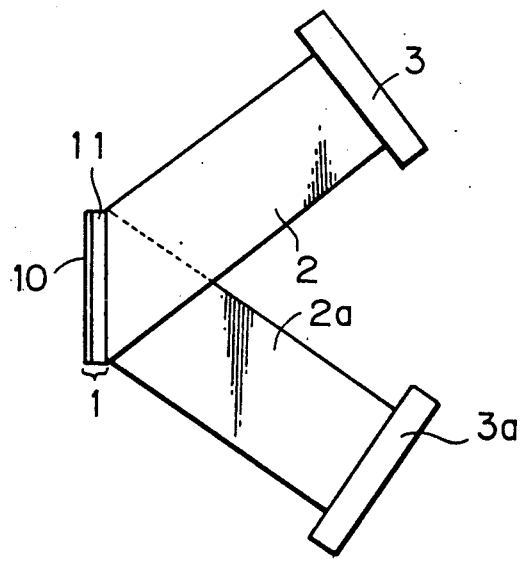

FIGS. 3 (A), 3 (B) and 3 (C) are plan views of arrangements of other examples of the present invention and illustrate the positional relationship among the fluorescent plate 1, the optical fiber bundles 2 and the CCD image pickup device 3. In the case of the arrangement shown in FIG. 3 (A), the bending angle of the optical fiber bundles 2 alternately distributed right and left is smaller than a right angle to make the fiber bundles 2 formed easily. The bundles 2 are preferably bent circularly.

In the case of the arrangement shown in FIG. 3 (B), the optical fiber bundles 2 are not bent but made straight so that their end surfaces are oblique to the axis of the fiber. As shown in the figure, the CCD image pickup devices 3 and 3a can be disposed on the same plane. This allows the CCD image pickup devices 3 distributed right and left to be secured and wired on the same wiring board for higher convenience. In the case of the arrangement shown in FIG. 3 (C), the axes of the optical fiber bundles are orthogonal to the image pickup surface of the CCD image pickup devices 3, but are oblique to the fluorescent surface 10. An inclination angle between the image pickup surface and the fluorescent surface 10 can be set to an appropriate value to the extent that the resolution in the lateral direction of the fluorescent surfaces 10 is not deteriorated.

To reproduce an image signal from each CCD image pickup device on the monitor screen, a sync signal from an oscillator (not shown) common to the CCD image pickup devices is used. The image signals of the individual CCD image pickup devices are combined in a monitor unit (not shown) and reproduced on a display (not shown) as images. At this time, the images of the individual CCD image pickup devices 3 are assigned to the vertical sections on the display. In addition, the images of the individual CCD image pickup devices are continuously developed horizontally on the display in synchronization with the radiographing apparatus's rotation angle around the jaw section, thus obtaining an entire X-ray panoramic image of the jaw section on the display.

Since the X-ray sensitivity of solid-state image pickup devices, such as CCD image pickup devices, is made generally high by properly selecting fluorescent material to be coated on the fluorescent plate, the intensity of the X-ray source can be made far smaller, 1/100 or less, than the intensity of the X-ray source for the film sensitivity method. As a result, the X-ray dose exposed to the patient can be reduced significantly.

We claim:

1. A medical X-ray image detecting device comprising a belt-shaped X-ray fluorescent plate disposed behind a slit formed by an X-ray shielding member, a plurality of optical fiber bundles, with the one end surface of each of the optical fiber bundles being attached to the fluorescent surface of the fluorescent plate, and solid-state image pickup devices, with the other end surface of each of the optical fiber bundles being attached to the image pickup surface of one of the image pickup devices, the X-ray image detecting device being characterized in that the fluorescent surface is divided in the longitudinal direction thereof into a plurality of rectangular units, the total length of which is the same as the vertical length of the image pickup surfaces of the image pickup devices, the one end surface of each of said optical fiber bundles is attached to one of said divided fluorescent surface units to make individual image formation possible, and said bundles are distributed alternately right and left in the longitudinal direction, said other end surface of each of said fiber bundles is attached to the image pickup surface of one of the image pickup devices disposed on the right/left side at the backward position of the fluorescent surface unit and behind said X-ray shielding member to make individual image formation possible, whereby the X-ray image on the whole fluorescent surface is detected by combining individual image signals obtained from the solid-state image pickup devices.

2. A medical X-ray image detecting device according to claim 1, wherein each of said optical fiber bundles is bent almost in the middle of the route thereof, the one end surface of each bundle is orthogonal to the axis of the fibers and is attached to said divided fluorescent surface unit, and the other end surface of each bundle is orthogonal to the axis of said fibers and is attached to the image pickup surface of a solid-state image pickup device.

3. A medical X-ray image detecting device according to claim 1, wherein each of said optical fiber bundles is straight, the one end surface of each bundle is oblique to the axis of the fibers and is attached to said divided fluorescent surface unit, and the other end surface of each bundle is orthogonal or oblique to the axis of said fibers and attached to the image pickup surface of a solid-state image pickup device.

* * * * *